(12) United States Patent
Pilon et al.

(10) Patent No.: US 8,957,018 B2
(45) Date of Patent: Feb. 17, 2015

(54) RECOMBINANT HUMAN CC10 PROTEIN FOR TREATMENT OF INFLUENZA

(75) Inventors: Aprile L Pilon, Gaithersburg, MD (US); Pierre Borgeat, Quebec (CA); Louis Flamand, Quebec (CA)

(73) Assignee: Therabron Therapeutics, Inc., Rockville, MD (US)

( * ) Notice: Subject to any disclaimer, the term of this patent is extended or adjusted under 35 U.S.C. 154(b) by 0 days.

(21) Appl. No.: 13/501,908

(22) PCT Filed: Oct. 13, 2010

(86) PCT No.: PCT/US2010/052527
§ 371 (c)(1), (2), (4) Date: Apr. 13, 2012

(87) PCT Pub. No.: WO2011/047065
PCT Pub. Date: Apr. 21, 2011

(65) Prior Publication Data
US 2012/0231997 A1 Sep. 13, 2012

Related U.S. Application Data

(60) Provisional application No. 61/252,028, filed on Oct. 15, 2009.

(51) Int. Cl.
A61K 38/17 (2006.01)
A61P 31/16 (2006.01)
C12N 5/02 (2006.01)
C07K 14/005 (2006.01)

(52) U.S. Cl.
CPC ..... *C07K 14/005* (2013.01); *C12N 2760/16122* (2013.01); *C12N 2760/16134* (2013.01)
USPC .......................................... 514/3.7; 435/375

(58) Field of Classification Search
None
See application file for complete search history.

(56) References Cited

U.S. PATENT DOCUMENTS

| | | | |
|---|---|---|---|
| 4,691,009 A | 9/1987 | Palmer | |
| 4,820,514 A | 4/1989 | Cummins | |
| 4,917,826 A | 4/1990 | Johnson | |
| 5,266,562 A | 11/1993 | Mukherjee | |
| 5,354,269 A | 10/1994 | Goodheart | |
| 5,470,885 A | 11/1995 | Fuhrman | |
| 5,482,930 A | 1/1996 | Wei | |
| 5,491,130 A | 2/1996 | Roberts | |
| 5,618,786 A | 4/1997 | Roosdorp | |
| 5,696,092 A | 12/1997 | Patierno | |
| 5,817,750 A | 10/1998 | Ruoslahti | |
| 6,066,724 A | 5/2000 | Ni | |
| 6,255,281 B1 | 7/2001 | Pilon | |
| 7,122,344 B2 | 10/2006 | Pilon | |
| 7,846,899 B2 | 12/2010 | Pilon | |
| 8,470,767 B2 | 6/2013 | Pilon | |
| 2002/0006640 A1 | 1/2002 | Ni | |
| 2002/0025510 A1 | 2/2002 | Strongin | |
| 2002/0160948 A1 | 10/2002 | Pilon | |
| 2002/0169108 A1 | 11/2002 | Pilon | |
| 2002/0173460 A1 | 11/2002 | Pilon | |
| 2003/0008816 A1 | 1/2003 | Pilon | |
| 2003/0109429 A1 | 6/2003 | Pilon | |
| 2003/0207795 A1 | 11/2003 | Pilon | |
| 2004/0047857 A1 | 3/2004 | Pilon | |
| 2005/0026139 A1 | 2/2005 | Fang | |
| 2005/0261180 A1 | 11/2005 | Pilon | |
| 2006/0025348 A1 | 2/2006 | Pilon | |
| 2006/0281681 A1* | 12/2006 | Pilon | ............................ 514/12 |
| 2008/0064633 A1 | 3/2008 | Pilon | |
| 2009/0029917 A1 | 1/2009 | Pilon | |
| 2009/0197808 A1 | 8/2009 | Pilon | |
| 2009/0227025 A1 | 9/2009 | Nichols | |
| 2009/0253174 A1 | 10/2009 | Serber | |
| 2010/0183640 A1 | 7/2010 | Pilon | |
| 2011/0183887 A1 | 7/2011 | Pilon | |
| 2011/0240012 A1 | 10/2011 | Pilon | |
| 2012/0231997 A1 | 9/2012 | Pilon | |

FOREIGN PATENT DOCUMENTS

| | | |
|---|---|---|
| WO | 9608572 | 3/1996 |
| WO | 9640657 | 12/1996 |

(Continued)

OTHER PUBLICATIONS

Levine CR, Gewolb IH, Allen K, Welch RW, Melby JM, Pollack S, Shaffer T, Pilon AL, Davis JM. The safety, pharmacokinetics, and anti-inflammatory effects of intratracheal recombinant human Clara cell protein in premature infants with respiratory distress syndrome. Pediatr Res 2005; 50:15-21.*

Centers for Disease Control. Influenza Antiviral Medication: A Summary for Clinicians. Aug. 30, 2011. p. 1-6. http://www.cdc.gov/flu/pdf/professionals/antivirals/clinician-antivirals-2011.pdf.*

Hay AJ, Gregory V, Douglas AR, Lin YP. The evolution of human influenza viruses. Phil Trans R Soc Lond. B (2001) 356, 1861-1870.*

Sarnsamak, P. TYpe-A (H1N1) virus attacks lungs. The Nation. Jul. 2009.*

Levine et al. Pediatric Res. 58(1);15-21:2005.*

(Continued)

*Primary Examiner* — Karlheinz R Skowronek
*Assistant Examiner* — Schuyler Milton
(74) *Attorney, Agent, or Firm* — Henry J. Cittone; Cittone & Chinta LLP (57) ABSTRACT

Methods of using recombinant human CC10 (rhCC10), also known as recombinant human uteroglobin, to reduce virus titers in the tissues of patients, particularly influenza titers in lung tissues are provided. RhCC10 may be used as a therapeutic in the treatment, cure, or prevention of viral infection, particularly influenza infection. More particularly, methods, including broadly the critical dosage ranges of rhCC10, intravenous and intranasal route of administration, which may be administered to treat, cure or prevent influenza infection are provided. Further provided are compositions useful in the foregoing methods and in administering rhCC10 to humans.

7 Claims, 6 Drawing Sheets

(56) References Cited

FOREIGN PATENT DOCUMENTS

| WO | 9701627 | 1/1997 | | |
|----|---------|--------|---|---|
| WO | 9853846 | 12/1998 | | |
| WO | 9952493 | 10/1999 | | |
| WO | WO 00/72868 | * | 6/2000 | ............ A61K 38/16 |
| WO | 00/72868 | 12/2000 | | |
| WO | 0179285 | 10/2001 | | |
| WO | 03003979 | 1/2003 | | |
| WO | 03057257 | 7/2003 | | |
| WO | 2007109118 | 9/2007 | | |
| WO | 2009140269 | 11/2009 | | |
| WO | 2011047065 | 4/2011 | | |

OTHER PUBLICATIONS

Abman et al., "Pathophysiology and Treatment of Bronchopulmonary Dysplasia: Current Issues." Pediatric Clinics of North America, vol. 41 No. 2, pp. 277-315 (1994).

Akiyama et al., "Fibronectin and Integrins in Invasion . . . " Cancer and Metastasis Reviews. vol. 14, pp. 173-189 (1995).

Andersson et al., "Heterologous Expression of Human Uteroglobin/ Polychlorinated Biphenyl-binding Protein." J. Biol. Chem., vol. 269 pp. 19081-19087 (1994).

Aoki et al., "Isolation of Human Uteroglobin from Blood Filtrate." Mol. Hum. Reprod., vol. 2, pp. 489-497 (1996).

Assmann et al., "Familial Glomerulonephritis Characterized by Massive . . . " Am. J. Kid. Dis., vol. 25, pp. 781-791 (1995).

Badcock, N.R. et al., "False-Positive EMIT.RTM.-st.TM. Ethanol Screen with Post-Mortem Infant Plasma", Clinical Chemistry, vol. 38, No. 3: 434-435 (1992).

Bischoff, et al Biochemistry 3013464-3472, 1991 Purification and Biochemical Characterization of Recombinant alphal-antilrypsin variants expressed in E. coli.

Bowton et al. Phospholipase A2 and arachidonate increase in bronchoalveolar lavage fluid after inhaled antigen challenge in asthmatics. Am J. Respir Crit Care Med. Feb. 1997; 155(2):421-5.

Camussi et al., J. Exp Med. Mar. 1, 1990:171(3):913-27, Abstract.

Chan C-C et al: "Effects of antiflammins on endotoxin-induced uveitis in rats" Archives of Ophthalmology, vol. 109, No. 2, Feb. 1991, pp. 278-281, XP000960732.

Chiesa M. et al., "Significant increase in immunoregulaton; protein blastokinin/uteroglobin in IgA/firbronectin complexes in sera of patients with IgA nephropathy", Nephrology Dialysis Transplantation, vol. 15, No. 9, 2000, p. A39 XP000971167.

Chilton et al. 1996. Antigen-induced generation of lysophospholipids in human airways. J. Exp. Med. 183: 2235-2245.

ClaraGen Inc. Press Release. Jun. 2, 1997—Claragen Explores How Uteroglobin Can Prevent Neonatal Lung Disease.

Clement; Rev Mal Respir Jul. 1996; 13(3):243-9.

Dennis E.A. Potential phopholipase A2s involved in inflammatow diseases. Agents Actions Suppl. 1995. vol. 46, pp. 3539, see p. 35, full para. 2.

Edelson et al. Acute lung injury induced by phospholipase A2: 2, 7 Structural and funcational changes. Am. Rev. Respir. Dis. May 1991, vol. 143, pp. 1102-1109, see p. 1102, col. 1, full paragraph 1, paragraphs bridging cols. 1-2 and cols. 2-3, paragraph bridging pp. 1105-1106.

Gonzalez et al. Biding of uteroglobin to microsomes and plasmatic membranes. FEBS Letters. 1995, vol. 361, pp. 225-258, see p. 257, Figure 4.

UniProt Basic UniProtKB Entry Viewer, Uter_Human. Oct. 1, 1989, Accession No. P11684.

Guy J. et al. Surfactant-producing rabbit pulmonary alveolar type Ii cells synthesize and secrete an anti-inflammatory protein, uteroglobin. Biochemical and Biophysical Research Communications, vol. 189, No. 2, Dec. 15, 1992, pp. 662-669, XP002153573.

Information Hyperlinked Over Proteins—SCGB1A1—secretglobin, family 1A, member 1 (uteroglobin), Last accessed 44 Dec. 2007.

Jarjour et al. Antigen-induced airway inflammation in atopic subjects generates dysfunction of pulmonary surfactant. Am J Respir Crit Care Med. Jul. 1999;160(1)1336-41.

Konstan et al. Effect of high-dose ibuprofen in patients with cystic fibrosis. N Engl J Med. Mar. 30, 1995;332 (13):848-54.

Kundu et al. Recombinant human uteroglobin suppresses cellular invasiveness via a novel class of high-affinity cell surface binding site, Proc. Natl. Acad. Sci U.S.A. Apr. 2, 1996, vol. 93, No. 7, pp. 2915-2919, see p. 2915. para. bridging cols. 1-2.

Lindhal et al., "Demonstration of different forms of lipocortin-1 and Clara cell protein-16 in human nasal and bronchoalveolar lavage fluids", Electrophoresis 20: 881-890 (1999).

Liu et al. Pulmonary surfactant given prophylactically alleviates an asthma attack in guinea-pigs. Clin Exp Allergy. Mar. 26, 1996; (3):270-5.

Lloret, S. et al., "Effect of Nonapeptide Fragments of Uteroglobin and Lipocortin I on Oedema and Mast Cell Degranulation", European Journal of Pharmacology vol. 264: 379-384 (1994).

Itoh et al. (1993), J Clin Lab Anal 7 (6): 394-400.

Lunardi-Iskandar, Y., et al. "Effects of a Urinary Factor from Women in Early Preganancy of HIV I, SID and associated Disease", Nature Medicine, vol. 4, No. 4, 428-434 (1998).

Makrides, Strategies for Achieving High-Level Expression of Genes in Escherichia coli, Microbiological Reviews, American Society for Microbiology, Washington, DC, US, vol. 60, No. 3, Sep. 1996, ISSN: 0146-0749 *p. 524*.

Manjunath, R. et al. "Inhibition of Thrombin-Induced Platelet Aggregation by Uteroglobin" Biochemical Pharmacology, vol. 36, No. 5-741-746 (1987).

Manjunath, R. et al., "Crosslinking of Uteroglobin by Transglutaminase" Biochemical and Biophysical Research Communications, vol. 121, No. 11 400-407 (1984).

MeSH Database, entry for "Cystic Fibrosis" [online] National Center for Biotechnology Information, National Library of Medicine, NIH, Apr. 8, 2008.

Miele, L. et al. "Novel Anti-Inflammatory Peptides From the Region of Higher Similarity Between Uteroglobin and Lipocortin I", Nature, vol. 335, No. 6192: 726-730 (1988).

Miele, L. et al., "High Level Bacterial Expression of Uteroglobin, A Dimeric Eukaryotic Protein with Two Interchain Disulfide Bridges, in its natural quaternary Structure" Journal of Biological Chemistry, vol. 265, No. 11: 6427-6435 (1990).

Miele, L., et al., "Uteroglobin: Structure, Molecular Biology, and New Perspectives on Its Function as a Phospholipase A$_2$ Inhlbitor" Endocrine Reviews, vol. 8, No. 4: 474-490 (1987).

Mihal, K., "One gene encoding three proteins with different functions," Am. J. Respir. Cell. Moi. Biol, vol. 5, pp. 1-3 (1991).

Mourot et al., Comparative Evaluation of Ultrafiltration Membranes for Purification of Synthetic Peptides, Separation Science and Technology, 1989, vol. 24, No. 5 & 6, pp. 353-367, especially pp. 353 and 354.

Mukerjee A B et al. "Could the Gene Coding for Human Uteroglobin (Clara Cell 10kDa Protein) be a candidate gene for Atopy?" American Journal of Human Genetics vol. 55 No. 3 pA197 (1994).

Mukherjee et al., "Modulation of Cellular Response to Antigens by Uteroglobin and Transglutaminase" Adv. Exp. Med. Biol., 231:135-152 (1988).

Mukherjee, A. et al., "Phospholipase A$_2$ Enzymes: Regulation and Physiological Role", Biochemical Pharmacology, vol. 48, No. 1: 1-10 (1994).

Nomori, H., et al. "Protein 1 and Clara Cell 10-kDa Protein Distribution in Normal and Neoplastic Tissued with Emphasis on the Respiratory System", Virchows Archives, vol. 424: 517-523 (1994).

Nord, M. et al., "Calcium-Dependent Binding of Uteroglobin (PCB-BP/CCSP) Two Negatively Charged Fossil Liposomes" EFEBS Letters vol. 374: 403-406 (1995).

Okutani, R. et al., "Simple and High-Yield Purification of Urine Protein 1 Using Immunoaffinity Chromatography: Evidence for the identity of Urine Protein 1 and Human Clara Cell 10-Kilodalton Protein", Journal of Chromatography, vol. 577: 25-35 (1992).

Olson et al. Know your neighbors: three phenotypes in null mutants of the myogenic bHLH gene MRF4. Cell Apr. 1996 5;85(1):14.

Pattabiraman et al., Crystal Structure Analysis of Recombinant Human Uteroglobin and Molecular Modeling of Ligand Binding, Ann. NY, Acad. Sci. 2000, vol. 923, pp. 113-127.

(56) References Cited

OTHER PUBLICATIONS

Peri et al., "Expression of Clara Cell 10-kD Gene in the Human Endometrium and its Relationship to Ovarian Menstrual Cycle," DNA and Cell Biology, 13(5):495-503 (1994).
Peter, W., "Recombinant Rabbit Uteroglobin Expressed at High Levels in *E. coli* Forms Stable Dimers and Binds Progesterone", Protein Engineering, vol. 3: 61-66 (1989).
Peteres et al, "Clinical determinants of abnormalities in pulmonary functions in survivors of . . . ," Am. Rev. Respir. Dis., vol. 139, pp. 1163-1168 (1989).
Piomelli, D., "Arachidonic Acid in Cell Signaling", Current Opinion in Cell Biology, 5: 274-180 (1993).
R&D Systems, Quantikine assay for IL-8 (Oct. 2004).
Boivin, G. et al., Rapid antiviral effect of inhaled zanamivir in the treatment of naturally occurring influenza in other wise healthy adults; J. of Infectious Diseases, Apr. 2000.
Johansson S. et al., Clara Cell Protein 16 (CC16) serum levels in infants during respiratory synctial virus infection, Acta Peadiatrica, Mar. 2009.
Bohn et al., Increased mortality associated with TCDD exposure in mice infected with influenza A virus is not due to severity of lung injury or alterations in Clara cell protein content, Chemic-Biological Interactions, Aug. 2005.
Fritz R Scott et al., Nasal cytokine and chemokine responses in experimental influenza A virus infection: Results of a placebo-controlled trial of intravenous zanamivir treatment, J. infectious Diseases, Sep. 1999.
EPO Supplementary Search Report, EP 10 82 4032, Feb. 2013.
Nord M, Schubert K, Cassel TN, Andersson O, Riise GC. 2002. Decreased serum and bronchoalveolar lavage levels of Clara cell secretory protein (CC16) is associated with bronchiolitis obliterans syndrome and airway neutrophilia in lung transplant recipients. Transplantation. 73(8):1264-9.
Ramsay PL, DeMayo FJ, Hegemier SE, Wearden ME, Smith CV, Welty SE. 2001. Clara cell secretory protein oxidation and expression in premature infants who develop bronchopulmonary dysplasia. Am J Respir Crit Care Med. 164(1):155-61.
Geerts L, Jorens PG, Willems J, De Ley M, Slegers H. 2001. Natural inhibitors of neutrophil function in acute respiratory distress syndrome. Crit Care Med. 29(10)1920-4.
Wang SZ, Rosenberger CL, Espindola TM, Barrett EG, Tesfaigzi Y, Bice DE, Harrod KS. 2001. CCSP modulates airway dysfunction and host responses in an Ova-challenged mouse model. Am J Physiol Lung Cell Mol Physiol. 281 (5):L1303-11.
Miller TL, Shashikant BN, Melby JM, Pilon AL, Shaffer TH, Wolfson MR. Recombinant human Clara cell secretory protein in acute lung injury of the rabbit: effect of route of administration. Pediatr Crit Care Med. Nov. 2005;6 (6):698-706.
Miller TL, Shashikant BN, Pilon AL, Pierce RA, Shaffer TH, Wolfson MR. Effects of an intratracheally delivered anti-inflammatory protein (rhCC10) on physiological and lung structural indices in a juvenile model of acute lung injury. Biol Neonate. 2006;89(3):159-70. Epub Oct. 6, 2005.
Shashikant BN, Miller TL, Welch RW, Pilon AL, Shaffer TH, Wolfson MR. Dose response to rhCC10-augmented surfactant therapy in a lamb model of infant respiratory distress syndrome: physiological, inflammatory, and kinetic profiles. J Appl Physiol. Dec. 2005;99(6):2204-11. Epub Aug. 4, 2005.
Mandal AK, Ray R, Zhang Z, Chowdhury B, Pattabiraman N, Mukherjee AB. Uteroglobin inhibits prostaglandin F2alpha receptor-mediated expression of genes critical for the production of pro-inflammatory lipid mediators. J Biol Chem. Sep. 23, 2005;280(38):32897-904. Epub Aug. 1, 2005.
Mattsson J, Remberger M, Andersson O, Sundberg B, Nord M. Decreased serum levels of clara cell secretory protein (CC16) are associated with bronchiolitis obliterans and may permit early diagnosis in patients after allogeneic stem-cell transplantation. Transplantation. May 27, 2005;79(10):1411-6.

Welty SE. CC10 administration to premature infants: in search of the "silver bullet" to prevent lung inflammation. Pediatr Res. Jul. 2005;58(1):7-9. Epub May 5, 2005.
Benson M, Jansson L, Adner M, Luts A, Uddman R, Cardell LO. Gene profiling reveals decreased expression of uteroglobin and other anti-inflammatory genes in nasal fluid cells from patients with intermittent allergic rhinitis. Clin Exp Allergy. Apr. 2005;35(4):473-8.
Johansson S, Keen C, Stahl A, Wennergren G, Benson M. Low levels of CC16 in nasal fluid of children with birch pollen-induced rhinitis. Allergy. May 2005;60(5):638-42.
Levine CR, Gewolb IH, Allen K, Welch RW, Melby JM, Pollack S, Shaffer T, Pilon AL, Davis JM. The safety, pharmacokinetics, and anti-inflammatory effects of intratracheal recombinant human Clara cell protein in premature infants with respiratory distress syndrome. Pediatr Res. Jul. 2005;58(1):15-21. Epub Mar. 17, 2005.
Ray R, Choi M, Zhang Z, Silverman GA, Askew D, Mukherjee AB. Uteroglobin suppresses SCCA gene expression associated with allergic asthma. J Biol Chem. Mar. 18, 2005;280(11):9761-4. Epub Jan. 27, 2005.
Yoshikawa S, Miyahara T, Reynolds SD, Stripp BR, Anghelescu M, Eyal FG, Parker JC. Clara cell secretory protein and phospholipase A2 activity modulate acute ventilator-induced lung injury in mice. J Appl Physiol. Apr. 2005;98 (4):1264-71. Epub Dec. 17, 2004.
Ye Q, Fujita M, Ouchi H, Inoshima I, Maeyama T, Kuwano K, Horiuchi Y, Hara N, Nakanishi Y. Serum CC-10 in inflammatory lung diseases. Respiration. Sep.-Oct. 2004;71(5):505-10.
Hung CH, Chen LC, Zhang Z, Chowdhury B, Lee WL, Plunkett B, Chen CH, Myers AC, Huang SK. Regulation of TH2 responses by the pulmonary Clara cell secretory 10-kd protein. J Allergy Clin Immunol. Sep. 2004;114(3):664-70.
Mandal AK, Zhang Z, Ray R, Choi MS, Chowdhury B, Pattabiraman N, Mukherjee AB. Uteroglobin represses allergen-induced inflammatory response by blocking PGD2 receptor-mediated functions. J Exp Med. May 17, 2004;199 (10):1317-30.
Iannuzzi MC. Clara cell protein in sarcoidosis: another job for the respiratory tract protector? Am J Respir Crit Care Med. Jan. 15, 2004;169(2):143-4.
Nosratabadi AR, Ljungman AG, Lindahl M, Welch R, Pilon A, Tagesson C. Clara cell 10-KDA protein inhibits endotoxin-induced airway contraction in isolated perfused rat lungs. Exp Lung Res. Oct.-Nov. 2003;29(7):455-73.
Ramsay PL, Luo Z, Major A, Park MS, Finegold M, Welty SE, Kwak I, Darlington G, Demayo FJ. Multiple mechanisms for oxygen-induced regulation of the Clara cell secretory protein gene. FASEB J. Nov. 2003;17(14):2142-4. Epub Sep. 18, 2003.
Wang SZ, Rosenberger CL, Bao YX, Stark JM, Harrod KS. Clara cell secretory protein modulates lung inflammatory and immune responses to respiratory syncytial virus infection. J Immunol. Jul. 15, 2003;171(2):1051-60.
Chandra S, Davis JM, Drexler S, Kowalewska J, Chester D, Koo HC, Pollack S, Welch R, Pilon A, Levine CR. Safety and efficacy of intratracheal recombinant human Clara cell protein in a newborn piglet model of acute lung injury. Pediatr Res. Oct. 2003;54(4):509-15. Epub Jun. 18, 2003.
Shijubo N, Kawabata I, Sato N, Itoh Y. Clinical aspects of Clara cell 10-kDa protein/ uteroglobin (secretoglobin 1A1). Curr Pharm Des. 2003;9(14):1139-49. Review.
Angert et al., CC10 reduces inflammation in meconium aspiration syndrome in newborn piglets, Pediatric Res. 2007 vol. 62, No. 6 pp. 684-688.
Yoshikawa S, Miyahara T, Reynolds SD, Stripp BR, Anghelescu M, Eyal FG, Parker JC. Clara cell secretory protein and phospholipase A2 activity modulate acute ventilator-induced lung injury in mice. J Appl Physiol. Apr. 2005;98 (4):1264-71.
Castro et al., Attenuation of Pulmonary Neuroendocrine Differentiation in Mice Lacking Clara Cell Secretory Protein, vol. 80, No. 10, p. 1533 (2000).
Kim et al., IL-13-induced Clara cell secretory protein expression in airway epithelium: role of EGFR signaling pathway, AJP—Lung 283:67-75, 2002. First published Feb. 22, 2002.
Liu et al, Gene expression profiles in human nasal polyp tissues studied by means of DNA microarray, J Allergy Clin Immunol, Oct. 2004 pp. 783-790.

(56) References Cited

OTHER PUBLICATIONS

Magdaleno et al, Interferon-gamma regulation of Clara cell gene expression: in vivo and in vitro, Am. Phys. Soc. 1997 L1142-L1151.
Widegren H, Andersson M, Greiff L., Effects of Clara cell 10 (CC10) protein on symptoms and signs of allergic rhinitis. Ann Allergy Asthma Immunol. Jan. 2009;102(1):51-6
Liu Z, Lu X, Zhang XH, Bochner BS, Long XB, Zhang F, Wang H, Cui YH, Clara cell 10-kDa protein expression in chronic rhinosinusitis and its cytokine-driven regulation in sinonasal mucosa, Allergy. Jan. 2009;64(1):149-57. Epub Dec. 12, 2008.
Johansson S, Keen C, Stahl A, Wennergren G, Benson M., Low levels of CC16 in nasal fluid of children with birch pollen-induced rhinitis. Allergy. May 2005;60(5):638-42.
Benson M, Fransson M, Martinsson T, Naluai AT, Uddman R, Cardell LO., Inverse relation between nasal fluid Clara Cell Protein 16 levels and symptoms and signs of rhinitis in allergen-challenged patients with intermittent allergic rhinitis. Allergy. Feb. 2007;62(2):178-83.
Benson M, Jansson L, Adner M, Luts A, Uddman R, Cardell LO., Gene profiling reveals decreased expression of uteroglobin and other anti-inflammatory genes in nasal fluid cells from patients with intermittent allergic rhinitis., Clin Exp Allergy. Apr. 2005;35(4):473-8.
Liu Z, Kim J, Sypek JP, Wang IM, Horton H, Oppenheim FG, Bochner BS., Gene expression profiles in human nasal polyp tissues studied by means of DNA microarray., J Allergy Clin Immunol. Oct. 2004;114(4):783-90.
Fritz SB, Terrell JE, Conner ER, Kukowska-Latallo JF, Baker JR., Nasal mucosal gene expression in patients with allergic rhinitis with and without nasal polyps., J Allergy Clin Immunol. Dec. 2003;112(6):1057-63.
Pilon, AL, Pilon, AL. The Development of Recombinant Human Uteroglobin/CC10 as a Therapeutic Agent in Inflammatory and Fibrotic Disease. Annals of the NYAS. vol. 293, pp. 280-299 (2000).
Farrow, J., Melby, J., Wiese, L., Lohnas, G., Welch, R., and Pilon, AL. Binding of rhCC10 to Fibronectin and Its Effect on Cellular Adhesion. Annals of the NYAS. vol. 293, pp. 338-342 (2000).
Mukherjee, A.B., Kundu, G.C., Mantile-Selvaggi, G., et al. Uteroglobin: a novel cytokine? Cellular and Molecular Life Sciences 55:771-787, (1999).
Matthews, J.H., Pattabiraman, N., Ward, K.B., Mantile, G., Miele, L. and Mukherjee, A.B. Crystallization and characterization of the recombinant human Clara cell 10-kDa protein. Proteins 20:191-196 (1994).
Zhang, Z., et al. Human Uteroglobin Gene: Structure, Subchromosomal Localization, and Polymorphism. DNA & Cell Biol. 16:73-83 (1997).
Peri, A., Cordella-Miele, E., Miele, L. and Mukherjee, A.B. Tissue-specific expression of the gene coding for human Clara cell 10- kD protein, a phospholipase A2-inhibitory protein. J Clin Invest 92:2099-2109 (1993).
Bernard, A., et al. Human urinary protein 1: Evidence for identity with the Clara cell protein and occurrence in respiratory tract and urogenital secretions. Clin. Chim. Acta 207:239-249 (1992).
Jackson, P.J. and R. Turner. Purification and Partial Amino Acid Sequence of Human Urine Protein 1: Evidence for Homology with Rabbit Uteroglobin. J. Chromatog. 452:359-367 (1988).
Levin, S.W., et al. Uteroglobin inhibits phospholipase A2 activity. Life Sci. 38:1813-1819 (1986).
Mantile, G., Miele, L., Cordella-Miele, E., Singh, G., Katyal, S.L. and Mukherjee, A.B. Human Clara cell 10-kDa protein is the counterpart of rabbit uteroglobin. J Biol Chem 268:20343-20351 (1993).
Vasanthakumar, G., et al. Inhibition of phagocyte chemotaxis by potent phospholipase A2 inhibitory protein, Uteroglobin. Biochem. Pharmacol. 37:389-394 (1988).
Lesur, O., et al. Clara Cell Protein (CC-16) Induces a Phospholipase A2-mediated Inhibition of Fibroblast Migration in Vitro. Am. J. Respir. Crit. Care Med. 152:290-297 (1995).
Dierynck, I.A., et al. 1996. The human Clara cell protein: biochemical and biological characterization of a natural immunosuppressor Multiple Schlerosis 1:385-387 (1996).

Leyton, J., et al. Recombinant human uteroglobin inhibits the in vitro invasiveness of human metastatic prostate tumor cells and the release of arachidonic acid stimulated by fibroblast-conditioned medium. Cancer Res., 54: 3696-3699 (1994).
Zhang, Z., et al. Severe Fibronectin-Deposit Renal Glomerular Disease in Mice Lacking Uteroglobin. 276:1408-1412 (1997).
Miele, L., Cordella-Miele, E., Mantile, G., Peri, A. and Mukherjee, A.B. Uteroglobin and uteroglobin-like proteins: the uteroglobin family of proteins. J Endocrinol Invest 17:679-692 (1994).
Johnston, C.J., et al. Altered Pulmonary Response to Hyperoxia in Clara Cell Secretory Protein Deficient Mice. Am. J. Respir. Cell Mol. Biol. 17:147-155 (1997).
Mango, G.W., et al. Clara cell secretory protein deficiency increases oxidant stress response in conducting airways. Am. J. Physiol. 275:L348-56 (1998).
Harrod, K.S., et al. Clara cell secretory protein decreases lung inflammation after acute virus infection. Am. J. Physiol. 275:L924-30 (1998).
Bernard, A.M., H.A. Roels, J.P. Buchet, and R.R. Lauwerys. Serum Clara cell protein: an indicator of bronchial cell dysfunction caused by tobacco smoking. Environ.Res. 66:96-104 (1994).
Bernard, A., et al. Clara cell protein in serum and bronchoalveolar lavage. Eur. Respir. J. 5:1231-1238 (1992).
Dhanireddy, R., T. Kikukawa, and A.B. Mukherjee. Detection of a rabbit uteroglobin-like protein in human neonatal tracheobronchial washings. BBRC 152:1447-1454 (1988).
Doyle, I.R., et al. Clearance of Clara Cell Secretory Protein 16 (CC16) and Surfactant Proteins A and B from Blood in Acute Respiratory Failure. Am. J. Respir. Crit. Care Med. 158:1528-1535 (1998).
Jorens, P., et al. Potential role of Clara cell protein, an endogenous phospholipase A2 inhibitor, in acute lung injury. Eur. Respir J. 8:1647-1653 (1995).
Hermans, C., and A. Bernard. Pneumoproteinaemia: a new perspective in the assessment of lung disorders. Eur. Respir. J. 11:801-803 (1998).
Van Vyve, et al. Protein content in bronchoalveolar lavage fluid of patients with asthma and control subjects. J. Allergy Clin. Immunol. 95:60-68 (1995).
Shijubo, et al. Serum Levels of Clara Cell 10-kDa Protein Are Decreased in Patients with Asthma. Lung 177:45-52 (1999).
Nomori, H., et al. Protein 1 (Clara Cell Protein) Serum Levels in Healthy Subjects and Patients with Bacterial Pneumonia. Am. J. Respir. Grit. Care Med. 152:746-750 (1995).
Dhanireddy, R., et al. Uteroglobin-like Protein in Premature Infants: Effect of Gestational Age. Ped. Res. 23:463A (1988).
Singh, G., and S.L. Katyal. Clara Cells and Clara Cell 10 kDa Protein (CC10). Am. J. Respir. Cell Mol. Biol. 17:141-143 (1997).
Dhanireddy, R., et al. Uteroglobin-like protein levels in premature infants on long term ventilator support. Ped. Res. 33:323A (1993).
Bernard, A., et al. Clara Cell Protein in Human Amniotic Fluid: A Potential Marker of Fetal Lung Growth. Ped. Res. 36:771-775 (1994).
Lopez de Haro, M.S., et al. Binding of retinoids to uteroglobin. FEBS Let. 349:249-251 (1994).
Singh, G. et al. Clara cell 10 kDa protein (CC10): comparison of structure and function to uteroglobin. Biochim. Biophys. Acta. 1039:348-355 (1990).
Pen, A., et al. Uteroglobin gene expression in the rabbit uterus throughout gestation and in the fetal lung: Relationship between uteroglobin and eicosanoid levels in the developing fetal lung. J. Clin. Invest. 96:343-353 (1995).
Davis, J.M. and Rosenfeld, W.N. Chronic Lung Disease. In: Neonatology:pathophysiology and Management of the Newborn, edited by Avery, G.B., Fletcher, M.A. and MacDonald, M.G. p. 453-477 (1994).
Whitsett, J.A., et al. Acute Respiratory Disorders. In: Neonatology:pathophysiology and Management of the Newborn, edited by Avery, G.B., Fletcher, M.A. and MacDonald, M.G. p. 429-452 (1994).
Stenmark, K., et al. Potential Role of Eicosanoids and PAF in the Pathophysiology of Bronchopulmonary Dysplasia. Am. Rev. Respir. Dis. 136:770-772 (1987).

(56) References Cited

OTHER PUBLICATIONS

Volovitz, B., et al. Relationship between leukotriene C4 and an uteroglobin-like protein in nasal and tracheobronchial mucosa of children. Implication in acute respiratory illnesses. Int. Arch Allergy Appl Immunol. 86:420-425 (1988).

Hermans, C., et al. Clara cell protein as a marker of Clara cell damage and bronchoalveolar blood barrier permeability. Eur. Respir. J. 13:1014-1021 (1999).

Lensmar, C., et al. Decreased pulmonary levels of the anti-inflammatory Clara cell 16 kDa protein after induction of airway inflammation in asthmatics. Cell. Mol. Life Sci. 57:976-981 (2000).

Lassus P, Nevalainen TJ, Eskola JU, Andersson S. Clara-cell secretory protein in preterm infants' tracheal aspirates correlates with maturity and increases in infection. Pediatr Pulmonol. 30(6):466-9 (2000).

Chen LC, Zhang Z, Myers AC, Huang SK. Cutting edge: altered pulmonary eosinophilic inflammation in mice deficient for Clara cell secretory 10-kDa protein. J Immunol. 167(6):3025-8 (2001).

Dierynck, I., et al. Potent inhibition of both human interferon-gamma production and biologic activity by the Clara cell protein, CC16. Am. J. Respir. Cell Mol. Biol. 12(2):205-10 (1995).

Shijubo N, Itoh Y, Yamaguchi T, Imada A, Hirasawa M, Yamada T, Kawai T, Abe S. Clara cell protein-positive epithelial cells are reduced in small airways of asthmatics. Am J Repir Crit Care Med. Sep. 1999;160(3):930-3.

Dhanireddy R, Kikukawa T, Mukherjee AB. Detection of a rabbit uteroglobin-like protein in human neonatal tracheobronchial washings. Biochem Biophys Res Commun. May 16, 1988;152(3):1447-54.

Khoor A, Gray ME, Singh G, Stahlman MT. Ontogeny of Clara cell-specific protein and its mRNA: their association with neuroepithelial bodies in human fetal lung and in bronchopulmonary dysplasia. J Histochem Cytochem. Dec. 1996;44(12):1429-38.

Miele L, Cordella-Miele E, Mantile G, Peri A, Mukherjee AB. Uteroglobin and uteroglobin-like proteins: the uteroglobin family of proteins. J Endocrinol Invest. Sep. 1994;17(8):679-92.

Johnston CJ, Mango GW, Finkelstein JN, Stripp BR. Altered pulmonary response to hyperoxia in Clara cell secretory protein deficient mice. Am J Respir Cell Mol Biol. Aug. 1997;17(2):147-55.

Mukherjee, A.B., E. Cordella-Miele, and L. Miele. 1992. Regulation of Extracellular Phospholipase A2 Activity: Implications for Inflammatory Diseases. DNA and Cell Biol. 11:233-243.

Wang SZ, Rosenberger CL, Bao YX, Stark JM, Harrod KS, Clara cell secretory protein modulates lung inflammatory and immune responses to respiratory syncytial virus infection, J Immunol. Jul. 15, 2003;171(2):1051-60.

Ikegami M, Harrod KS, Whitsett JA, Jobe AH, CCSP deficiency does not alter surfactant homeostasis during adenoviral infection, Am J Physiol. Nov. 1999;277(5 Pt 1):L983-7.

Harrod KS, Mounday AD, Stripp BR, Whitsett JA, Clara cell secretory protein decreases lung inflammation after acute virus infection, Am J Physiol. Nov. 1998;275(5 Pt 1):L924-30.

Search Report and Written opinion for PCT/us2010/052527 dated Jan. 5, 2011.

Hendrickson et al., Development of Lentiviral Vectors with Regulated Respiratory Epithelial Expression In Vivo, Am. J. Resp. Cell & Molec. Bio. 2007 37(4); 414-423, Tables 1&2.

Murakami et al. Mini-plasmin found in the epithelial cells of bronchioles triggers infection by broad spectrum influenza A viruses and Sendai virus. Eur. J. of Biochem. 2001, 268:2847-2855; p. 2853, col. 2, pra 1 to p. 2854 col. 1 para 3.

Endo et al., Growth of Influence a Virus in Primary, Differentiated Epithelial Cells Derived from Adenoids, Am. Soc. for Micro. 1996, 70(3):2055-2058; p. 2057.

Islam et al., Acquisition of Pathogenicity of a Newcastle Disease Virus Isolated from a Japanese Quail by Intracerebral Passage in Chickens, JP J. of Vet. Res. 1995 42(3-4):147-156; Abstract, Tables 3-5.

Ray, M. et al. "Cloning and Characterization of the Mouse Clara Cell Specific 10 kDa Protein Gene Comparison of the 5'-Flanking Region With the Human Rat and Rabbit Gene", Biochemical and Biophysical Research Communications, vol. 197, No. 1: 163-171 (1993).

Rennard et al., "Production of Fibronectin by the Human Alveolar Macrophase: Mechanism for the Recruitment of Fibroblasts to Sites of Tissue Injury in Interstitial Lung Diseases" Proc. Natl. Acad. Sci. USA, 78(11): 7147-7151 (1988).

Ricci et al. (2004), Curr. Pharm. Des, 10(31): 3901-3911.

Robinson, D., "Macromolecular Transport in Rabbit Blastocysts: Evidence for a Specific Uteroglobin Transport System", Molecular and Cellular Endocrinology, 63: 227-237 (1989).

Ruoslahti et al, "Fibronectin and Its Receptors," Ann. Rev. Biochem, vol. 57, pp. 374-413 (1988).

Scheuer, W., "Phospholipase A2-regulation and inhibition," Klin Wochenschr, vol. 67, pp. 153-159 (1989).

Scopes R K (1994) Protein Purification Principles and Practice 3rd Edition (Cantor C R ed) pp. 270-277 Springer-Verlag, New York.

Shijubo, N. et al. "Serum and BAL Clara Cell 10 kDa Protein (CC10) Levels and CC10-Positive Bronchiolar Cells Are Decreased in Smokers", European Respiratory Journal, vol. 10: 1108-1114 (1997).

Shimizu et al. (1997), Biol. Pharm. Bull. 20(12)l 1219-1223.

Shin et al., Enhanced Production of Human Mini-Proinsulin in Fed-Batch Cultures at High Cell Density of *Escherichia coli* BL21(DE3)(pET-3aT2M2], Biotechnol. Prog. 1997, vol. 13, pp. 249-257, especially p. 249.

Singh et al, "Identification, Cellular Localization, Isolation, and Characterization of Human Clara Cell-Specific 10 KD Protein," J. Hist. Cyt, vol. 36, pp. 73-80 (1988b).

Singh, G. et al. "Mouse Clara Cell 10-kDa (CC10) Protein: cDNA Nucleotide Sequence and Molecular Basis for the Variation of Progesterone Binding of CC10 from Different Species", Experimental Lung Research vol. 19: 67-75 (1993).

Singh, G., et al., "Isolation and Amino Acid Composition of the Isotypes ofa Rat Clara Cell Specific Protein", Experimental Lung Research, 133299-309 (1987).

Sipes et al. (1993), J. Cell. Biol. 121(2); 469-477.

Steward el al. (2002), J. Mol Biol. 318i 935-940.

Stripp et al, "Clara cell secretory protein: a determinant of PCB bioaccumulation in mammals," Am. J. Physiol., 271 (Lung Cell Mol. Physiol. 15), pp. L656-L664 (1996).

Stripp et al, "Plasticity of airway cell proliferation and gene expression after acute naphthalene injury," Am. J. Physiol., vol. 269, pp. L791-L799 (1995).

Stripp, B. et al. "Structure and Regulation of the Murine Clara Cell Secretory Protein Gene", Genomics vol. 20: 27-35 (1994).

Stripp, B. et al., "cis-Acting Elements That Confer Lung Epithelial Cell Expression of the CC.sub.10 Gene", Journal of Biological Chemistry, vol. 267, No. 21: 14703-14712 (1992).

Torkkeli et al., Uterine and lung uteroglobins in the rabbit. Two similar proteins with differential hormonal regulation Biochem Biophys Act. 1978, vol. 544, No. 3, pp. 578-592, especially pp. 580-581.

Tykka et al. A randomized double-blind study using CaNa2EDTA, a phospholipase A2 inhibitor, in the management of human acute pancreatitis. Scan. J. Gastroenterology, (Jan. 1985) 20 (1) 5-12.

Tykka et al. Phospholipase A2 inhibitors and their possible clinical use in the treatment of acute pancreatitis. Scand J Gastroenterol 1980;15(5):519-28, Abstract only.

Umland et al, "Structure of human Clara cell phopholipid-binding protein-ligand complex at 1.9 A resolution," Nature Struct. Biol., vol. 1, pp. 538-545 (1994).

Umland et al, "Twixt form and function," Nat. Struct. Biol, vol. 2, pp. 919-922 (1995).

UniProt Accession No. P10145 (IL8_Human. Jul. 1, 1989).

Vadas et al, "Potential therapeutic efficacy of inhibitors of.,.," Agents Actions, vol. 19, pp. 194-202 (1986).

Van Bisbergen et al, "Synthetic peptide from lipocortin 1 has no phospholipase inhibitory activity," FEBS Lett., vol. 247, pp. 293-297 (1989).

Van Winkle, L. et al., "Repair of Naphthalene-Injured Microdissected Airways In vitro" American Journal of Respiratory Cell and Molecular Biology, vol. 15: 1-8 (1996).

Vostal, J. et al. "Novel Peptides Derived From a Region of Local Homology Between Uteroglobin and Lipocortin-1 Inhibit Platelet

(56) References Cited

OTHER PUBLICATIONS

Aggregation and Secretion", Biochemical and Biophysical Research Communications, vol. 165, No. 1: 27-36 (1989).

Watts et al., "Effect of Dexamethasone Therapy on Fibronectin and Albumin Levels in Lung Secretions of Infants with Bronchopulmonaw Dysplasia" J. Pediat. 121: 597-607 (1992).

Wolf et al. (1992), Hum MOl Genet 1(6)1 371-378.

Wu, C. et al. "Integrin Activation and Cytoskeletal Interaction Are Essential for the Assembly of a Fibronectin Matrix", Cell, vol. 83: 715-724 (1995).

Wuenschell, C. et al., "Embryonic Mouse Lung Epithelial Progenitor Cells Co-Express Immunohistochemical Markers of Diverse Mature Cell Lineages", The Journal of Histochemistry and Cytochemistry, vol. 44, No. 2: 113-123 (1996).

Zhang et al, "Modulation of Cell Surface Fibronectin Asembly Sites by Lysophosphatidic Acid," J. Cell Biol., vol. 127, pp. 1447-1459 (1994).

Zhang, Q. et al., "Cross-linking of the NH$_2$—Terminal Region of Fibronectin to Molecules of Large Apparent Molecular Mass", The Journal of Biological Chemistry vol. 271, No. 52: 33284-33292 (1996).

* cited by examiner

RECOMBINANT HUMAN CC10 PROTEIN FOR TREATMENT OF INFLUENZA

CROSS REFERENCE TO RELATED APPLICATIONS

This application is a continuation-in-part of PCT International Application No. PCT/US10/52527, filed Oct. 13, 2010, which claims the benefit of U.S. Provisional Application No. 61/252,028, filed Oct. 15, 2009, the disclosures of each of which are incorporated herein by reference in their entirety.

FIELD OF THE INVENTION

Embodiments of the present invention relate to methods of reducing viral titers in vivo and treating a viral respiratory infection in a patient. Embodiments of the present invention also relate to methods of treating influenza infection, including Type A influenza, particularly H1N1 influenza. Furthermore, embodiments of the present invention also relate to methods of treating the above using intranasally-administered and/or intravenously- administered, and/or inhaled recombinant human CC10.

BACKGROUND

Clara Cell "10 kDa" protein (CC10) or uteroglobin (UG) is a small, homodimeric secretory protein produced by several mucosal epithelia and other organs of epithelial origin (Mukherjee, 1999). CC10 consists of two identical subunits of 70 amino acid residues, each with the "four helical bundle" secondary structure motif, joined in antiparallel orientation by two disulfide bonds between Cys 3 and 69', 3' and 69 (Matthews, 1994;

Morize, 1997). CC10 is the first member of an emerging family of small globular proteins that share the same secondary, tertiary and quaternary structure and are thought to mediate similar functions. The homodimer containing two disulfide bonds appears to be its primary form. In humans, the lung is the main site of CC10 production, while several other organs synthesize smaller amounts of mRNA encoding this protein (Singh, 1987; Sandmoller, 1994). CC10 is an anti-inflammatory and immunomodulatory protein that has been characterized with respect to various interactions with other proteins, receptors and cell types (reviewed in Mukherjee, 1999 and Pilon, 2000). Lower levels of CC10 protein or mRNA have been found in various tissue and fluid samples for a number of clinical conditions characterized by some degree of inflammation including pneumonia (Nomori, 1995).

The physiology of CC10 protein in different types of pulmonary infections has been studied in one strain of CC10 knockout mouse. In two studies in which CC10 knockout and wild type mice were each infected with either Pseudomonas aeruginosa or adenovirus, two common human respiratory pathogens, the wild type mice experienced more rapid clearing of the pathogens, with greater killing of the pathogens by the innate immune system, suggesting a benefit to CC10 deficiency during viral and bacterial infection (Hayashida, 1999; Harrod, 1998). This is consistent with earlier observations in which CC10 was reported to be an immunosuppressive agent (Dierynck, 1995; 1996), indicating that CC10 would suppress the natural immune response to an infection, whether bacterial or viral, including influenza. Thus, the administration of CC10 in the presence of a viral or bacterial respiratory infection could not be expected to benefit the patient. Subsequently, it was reported that restoration of CC10 function using recombinant human CC10 protein (rhCC10) prior to infection with respiratory syncytial virus (RSV), enabled a more rapid clearance of the infection than in untreated knockout mice (Wang, 2003). However, a recent study showed that rhCC10 can prevent the development of acquired immunity, specifically antigen-specific T cells, when present at the same time that dendritic cells are exposed to antigen (Johansson, 2007), which again indicates that administration of rhCC10 may not benefit a patient with an infection. Thus, the current state of knowledge regarding the potential hazards or benefits of rhCC10 treatment during a respiratory infection is conflicting and allows no conclusions to be drawn regarding the safe and/or efficacious use of CC10 to treat different types of respiratory infections. No information regarding the effect of CC10 on influenza infection is available. We report herein, direct verification of the efficacy of rhCClO against influenza Type A in vivo, direct verification of the anti-viral effects of CC10 at the cellular level, its mechanism of action, and its potential use to treat and/or prevent viral infection, and, in particular, influenza infection.

Influenza has caused four major outbreaks (1889, 1918, 1957, and 1968) in the past 120 years, causing the deaths of an estimated 50-100 million people worldwide. Influenza is an orthomyxovirus, an RNA virus that is transmitted by aerosols as well as by direct contact of contaminated surfaces with nasal mucosa and targets respiratory epithelial cells. Influenza infection may cause severe symptoms, including fever, sore throat and muscle aches, malaise, weight loss, respiratory congestion, and sometimes respiratory failure and death. Influenza elicits an acquired immune response (cytotoxic T cells and antibodies) that typically clears the infection in 1-2 weeks in normal healthy individuals. Several subtypes of influenza that infect humans, including avian influenza (H5N1), seasonal influenza H3N2, and swine flu (H1N1), can be treated with antiviral agents such as neuraminidase inhibitors. However, the rapid rate of mutation in influenza has led to the development of drug-resistant strains (Moscona, 2009), such that widespread use of antiviral agents for prevention and or treatment will lead to acceleration of the development of resistance to these drugs. New therapeutic agents are therefore needed to treat, cure and prevent influenza infection. Likewise, there are no approved therapies for the vast majority of viral infections in the respiratory tract and other body systems.

OBJECTS OF THE INVENTION

The foregoing provides a non-exclusive list of the objectives achieved by embodiments the present invention:

It is an object of embodiments of the invention to reduce pulmonary viral titer and thereby treat, cure or prevent influenza infection, especially Type A influenza infection, and more especially strain H1N1 influenza infection.

It is a further object of embodiments of the invention to reduce pulmonary viral titer and treat, cure, or prevent influenza infection by administering CC10 by the intravenous route, the inhaled route, or the intranasal route (according to PCT 2009), or by a combination of routes.

It is another object of embodiments of the invention to reduce viral titer and treat, cure, or prevent viral infection by administering CC10 by the intravenous route, the inhaled route, or the intranasal route, the oral route, the intravaginal route, or by a combination of routes.

It is yet another object of embodiments of the invention to inhibit viral replication at the cellular level using CC10 or other members of the secretoglobin family.

SUMMARY OF THE INVENTION

These and other objects, features and advantages are achieved by embodiments of the invention by administering rhCC10 in a dosage range given at appropriate intervals, or in one dose, to reduce viral titer and treat, cure or prevent viral infection.

These and other objects, features and advantages are also achieved by embodiments of the invention by administering CC10 in a dosage range given at appropriate intervals or in one dose where a patient is diagnosed with a viral infection by symptoms characteristic of the particular virus, and/or by detection of virus in patient samples through culturing of the virus, immunological detection of the virus, and/or detection of the viral nucleic acid, using standard methods.

These and other objects, features and advantages are also achieved by embodiments of the invention by administering CC10 in a dosage range given at appropriate intervals or in one dose where a patient is diagnosed with an influenza infection by symptoms of fever, myalgia, and congestion, and/or by detection of influenza virus in patient samples (nasal lavages, blood or sputum samples) through culturing of the virus, immunological detection of the virus, and/or detection of the viral nucleic acid, using standard methods.

In certain aspects of the invention, CC10 is administered intranasally in a dose divided about equally between each nostril in a range of 1.5 micrograms to 1.5 milligrams per kilogram of body weight per day, or in multiple doses which taken together achieve this dosage range on a daily basis to reduce pulmonary viral titer and treat, cure or prevent influenza infection.

In another aspect, CC10 is administered intravenously in a dose of up to 10 milligrams per kilogram of body weight per day, or in multiple doses which taken together achieve this dosage range on a daily basis to treat, cure or prevent influenza infection.

In another aspect, a non-human CC10 protein is administered in a dosage range given at appropriate intervals or in one dose where a patient is diagnosed with a viral infection by symptoms characteristic of the particular virus, and/or by detection of virus in patient samples through culturing of the virus, immunological detection of the virus, and/or detection of the viral nucleic acid, using standard methods.

In yet another aspect, another member of the CC10 family of proteins, collectively known as secretoglobins, is administered in a dosage range given at appropriate intervals or in one dose where a patient is diagnosed with a viral infection by symptoms characteristic of the particular virus, and/or by detection of virus in patient samples through culturing of the virus, immunological detection of the virus, and/or detection of the viral nucleic acid, using standard methods.

DETAILED DESCRIPTION

Embodiments of the present invention relate to the use of CC10 to reduce pulmonary viral titer and treat, cure or prevent influenza infection. The CC10 is preferably a recombinant human CC10 protein (rhCC/0) obtained by the processes described in U.S. Patent App. Publication No.: 20030207795 and PCT/US09/43613 attached hereto at Exs. A and B respectively, all of which are incorporated by reference in their entirety, or via any other process which yields pharmaceutical grade rhCC10. The rhCC10 of the embodiments of the present invention may be administered with, without, before or after other intranasal, pulmonary, or systemic therapy.

Without limiting the scope of possible synthetic processes that may be used to make human CC10, the recombinant human CC10 (aka uteroglobin) that is active in suppressing viral replication in vitro and in vivo was synthesized and characterized as described in U.S. Patent App. Publication No.: 20030207795.

Preparations of rhCC10 for intranasal administration as described in PCT/US09/43613 represent further embodiments of the present invention that may be used to suppress viral replication in vivo, particularly in the nasal passages and sinuses.

Dosages

Preferably, in treating or preventing influenza infection, rhCC10 is administered intranasally, to each nostril 1-3 times per day, for 7-14 days, and every other day thereafter for another 14 days, and thereafter as needed. More preferably, rhCC10 is administered as soon as the patient begins to experience fever, myalgia, and congestion or is diagnosed with influenza.

The rhCC10 may be produced in a process comprising the steps of: a) providing a bacterial expression system capable of expressing rhCC10; b) inoculating a fermenter with an inoculum comprising the bacterial expression system to form a fermentation culture; c) adding an induction agent to the fermentation culture to induce the expression of rhCC10 by the bacterial expression system; d) harvesting the rhCC10 expressed in step c; and e) purifying the rhCC10 harvested in step d, wherein the purifying step comprises the use of at least one filter and at least one ion exchange column, as described in U.S. Patent App. Publication No.: 20030207795. The rhCC10 may also be expressed in alternative bacterial, fungal, insect, mammalian, or plant expression systems and purified to meet specifications for a pharmaceutical product suitable for administration to humans using standard methods.

Specifications and testing results for pharmaceutical grade rhCC 10, according to U.S. Patent App. Publication No.: 20030207795, that may be used to reduce viral titers include the following:

| Test | Specification |
|---|---|
| Color | Clear, colorless |
| Appearance | No turbidity |
| Homogeneity | Homogeneous |
| Purity | ≥95% |
| Aggregation | ≤5% |
| Sterility | Sterile |
| Biological activity | Positive |
| Bacterial nucleic acid | <100 pg/dose |
| Mass spectroscopy | App 16110 |
| pH | 5-8 |
| Isoelectric focusing | 4.7 +/− 1 |
| Free Thiol | <10% (w/w) |
| LAL | <5 EU/mg |
| Copper | <16 µM |

In a further embodiment, the rhCC10 of the present invention that inhibits viral replication also inhibits phospholipase $A_2$ ($PLA_2$) enzymes, as described in U.S. Patent App. Publication No.: 20030207795.

To effectuate the desired outcomes which are further described below, reference is made to methods of administration described in the following embodiments:

In one embodiment, a dose or multiple doses of intranasal rhCC10 equaling a dose ranging from about 1.5 micrograms to about 5 milligrams per kilogram of body weight per day may be administered. In another embodiment, rhCC10 may be administered in the dose range on a daily basis. In yet another embodiment, rhCC10 may be administered in the dose range on a daily basis for at least seven days consecutively. In still a further embodiment, rhCC10 may be administered in the dose range on a daily basis for at least 14 days consecutively. In still another embodiment, rhCC10 may be administered in the dose range every other day for 30 days consecutively. In yet another embodiment, rhCClO may be administered in tapered dosages daily for ten consecutive days, said tapered dosages comprising a high dose at each administration for the first three days, an intermediate dose at each administration for the second three days, and a low dose at each administration for the last four days. In yet still another embodiment, rhCC10 may be administered in the dose range or in tapered doses up to three times per day, approximately every eight hours.

In another embodiment, the above doses of rhCC10 may be administered intranasally to the patient as an aerosol, by intranasal spray or lavage, or by deposition of a gel or cream, or other method of instillation in the nasal passages.

In another embodiment, the above doses of rhCC10 may be administered by inhalation to the patient as an aerosol, by nebulizer or metered dose inhaler, or other method of direct application to the lungs and airways.

In another embodiment, in treating or preventing influenza infection, rhCC10 is administered intravenously, in doses of 15 micrograms to 20 milligrams per kilogram of body weight, 1-3 times per day, for 7-14 days, and every other day thereafter for another 14 days, and thereafter as needed. In yet another embodiment, rhCC10 may be administered in tapered dosages daily for ten consecutive days, said tapered dosages comprising a high dose at each administration for the first three days, an intermediate dose at each administration for the second three days, and a low dose at each administration for the last four days. In yet still another embodiment, rhCC10 may be administered in the dose range or in tapered doses up to three times per day, approximately every eight hours.

In another embodiment the above doses of rhCC10 may be administered to the patient using a combination of intranasal, inhaled, and intravenous routes. In a further embodiment, rhCC10, in accordance with the methods described above, may be administered prior to, during or after anti-viral therapy, anti-biotic therapy, decongestant, anti-histamine, mucolytic, expectorant, mucus suppressor, surfactant, bronchodilator, vasoconstrictor, sinus pain analgesic, or other typical therapy. In still another embodiment, rhCClO, in accordance with the methods described above, may be administered to reduce pulmonary viral titer and treat, cure, or prevent influenza infection.

The doses of rhCC10 and application methods described above may be administered daily, more than once daily, three times daily, every other day or in a tapered fashion depending upon the severity of influenza infection being treated, the patient's overall health, and whether underlying conditions are present. For example, the more severe the infection, the higher the amount of rhCC10 would be required to effectively treat it. It is understood that a physician would be able to monitor and adjust doses, formulations, and application methods as needed based on the patient's symptoms and responses to therapy and within the parameters and dose ranges described in the embodiments of the present invention.

Formulations

Intranasal formulations, devices, and methods by which rhCC10 may be administered intranasally have been described in PCT/US09/43613, which is incorporated herein by reference in its entirety. The intravenous formulation of rhCC10 consists of a 5.5 mg/ml solution in 0.9% saline and has been described in U.S. Patent App. Publication No.: 20030207795, which is incorporated herein by reference in its entirety.

EXAMPLE 1

Propagation and Titer Determination of Influenza Virus

The A/PR/8/34 Influenza A viral strain (H1N1), purchased from the American Type Culture Collection (Manasass, Va., USA) is prepared. Influenza virus is propagated in MDCK cells (ATCC catalog# CCL-34) by infecting 60% confluent cell monolayer (150 cm$^2$ flasks) with flu virus at a multiplicity of infection (MOI) of 0.01. Three to four days later, when cytopathic effect is generalized and most of the cells have detached from the culture vessel, the cells and supernatants are harvested. Cells are removed by centrifugation (800 g) and the supernatant filtered (0.45 µm) and centrifuged (18000 g) for 2 hours at 4° C. to pellet viruses. The viral pellet is resuspended in DMEM medium, aliquoted and stored at −150° C. Influenza virus titer is determined by applying 0.1 mL of serially diluted viral stocks to MDCK cell monolayers in a 96-well plate cultured in the presence of 0.1% bovine serum albumin and trypsin. Three days later, cytopathic effects were scored and the tissue culture infectious dose 50% ($TCID_{50}$) is determined using Karber's method.

Processing of Lung Tissues for viral load analysis. Sections of the left and right lobes from lungs of infected mice and cotton rats are aseptically removed, weighed and homogenized in 1 ml of DMEM medium for 45 seconds using a tissue tearor apparatus (model#985-370, Biopspec Products Inc.) at a setting of 5. Homogenates are centrifuged at 3000g for 20 minutes. Clarified supernatants are collected, and stored frozen at −150° C. until used.

Determination of Viral Titers. Viral titers in amplified viral stocks and in lung homogenates were determined by serial dilution followed by plaque forming assay (PFA) or foci forming assay (FFA). Plaque forming units (PFU) and foci forming units (FFU) per milliliter of original sample were calculated prior to the start of the study. One set of influenza samples sufficient for carrying out PFA and FFA was stored and PFU and FFU were determined after the completion of the studies. Serial dilutions of cultured virus in clarified media (DMEM with 1% BSA) were prepared across $10^1$ to $10^8$ dilution range. Each dilution is evaluated by a plaque forming assay (PFA) and a foci forming assay (FFA). Culture titers typically yield $10^7$-$10^9$ pfu/ml for influenza.

EXAMPLE 2

Intranasal Administration of rhCC10 to Reduce Pulmonary Influenza Virus Titer The cotton rat (*S. hispidus*), a type of vole, is an animal model in which influenza replicates and generates a mild respiratory infection (Ottolini, 2005). The animals are infected by intranasal inoculation with influenza virus and pulmonary viral titers peak two days (about 48 hours) after inoculation. This model is used to screen for compounds that inhibit influenza replication in vivo.

Figure 1:
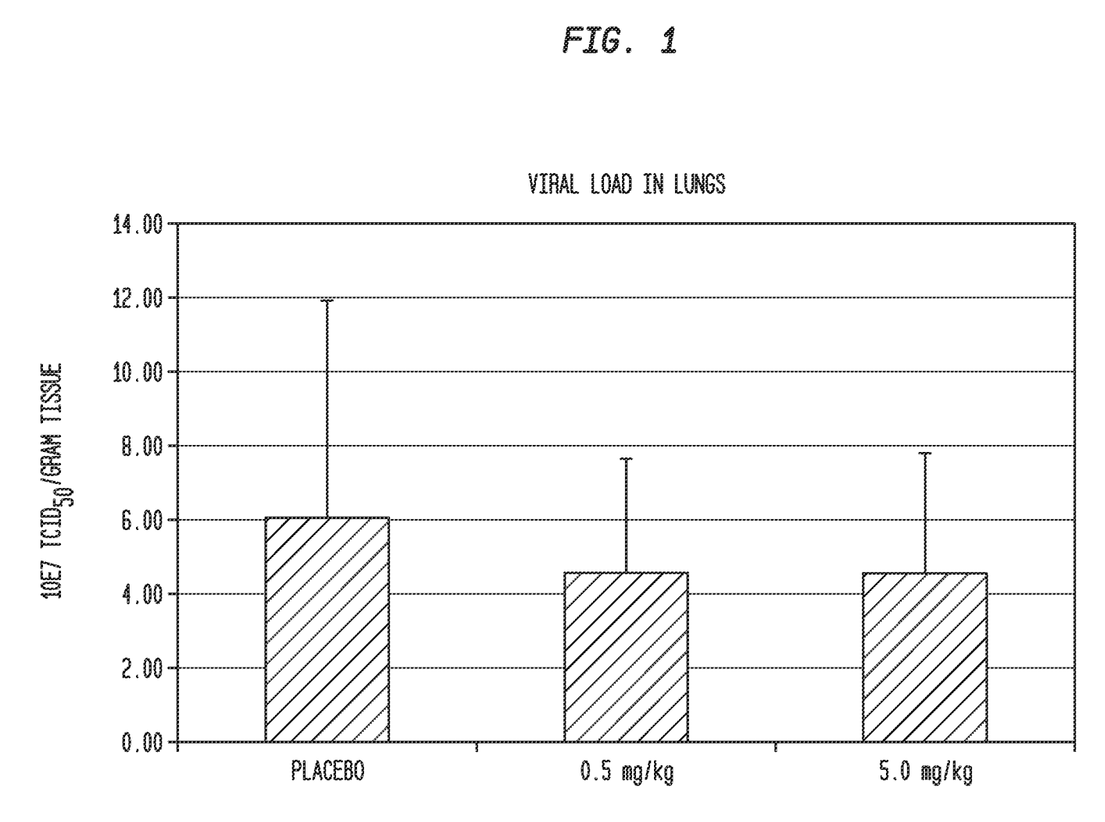
FIG. 1 is a bar graph depicting H1N1 viral load at 2 days in lungs of infected cotton rats treated with intranasal rhCC 10. Viral titer is expressed as (x 107) TCID50/gram of tissue.

Pathogen free cotton rats were purchased from Virion Systems, Inc. (Rockville, Md.). A total of eighteen cotton rats (*S. hispidus*, 6-8 weeks old) were infected with Type A influenza (A/PR/8/34), strain H1N1, by intranasal inoculation using $10^7$ TCID$_{50}$ in 0.1 ml volume for 275 each rat. Six animals received a placebo (0.9% NaCl), six animals received 0.5 mg/kg of rhCC10 and six animals received 5.0 mg/kg of rhCC10 by intranasal instillation 2 hours before viral inoculation. Animals were sacrificed on day 2 post-infection when viral titers are typically highest and viral load was determined in lung tissue. FIG. 1 illustrates the reductions in viral titer in lung tissue that were observed in the both rhCC10 dose groups. Viral titer in lung is expressed as (x $10^7$) TCID$_{50}$/gram of tissue.

EXAMPLE 3

Systemic Administration of rhCC10 to Reduce Pulmonary Influenza Virus Titer

Figure 2:
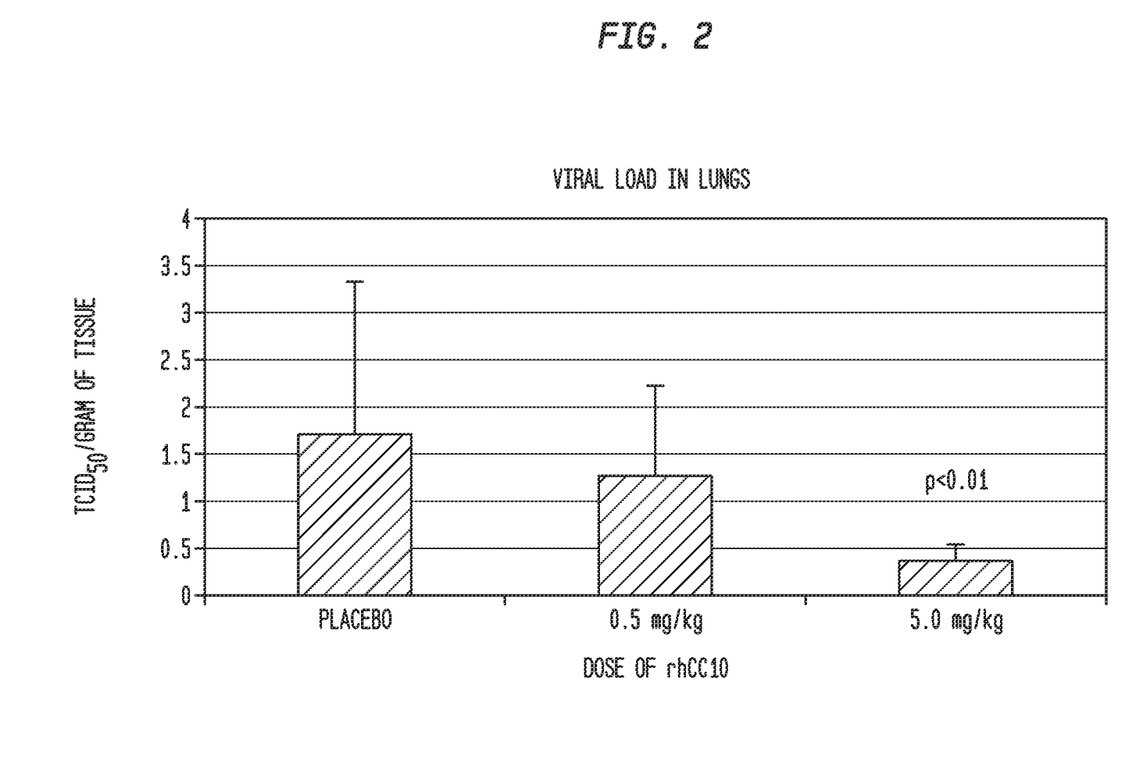
FIG. 2 is a bar graph depicting H1N1 viral load at 2 days in lungs of cotton rats treated with intraperitoneal injection of rhCC 10. Viral titer is expressed as (x 107) TCID50/gram of tissue.

A total of eighteen cotton rats (*S. hispidus*, 6-8 weeks old) were infected with Type A influenza (A/PR/8/34), strain H1N1, by intranasal inoculation using $10^7$ TCID$_{50}$ in 0.1 ml volume for each rat. Six animals received a saline placebo, six animals received 0.5 mg/kg of rhCC10 and six animals received 5.0 mg/kg of rhCC10 by intraperitoneal injection (IP). The IP route results in significant amounts of circulating rhCC10 and simulates the intravenous route of administration in humans. Each animal received a total of six doses of either placebo or rhCC10 approximately every 12 hours, including two doses (morning and afternoon) on the day before infection, two doses on the day of infection, and two doses on the day after infection (3 doses before infection, 3 doses after infection). Animals were sacrificed on day 2 post-infection when viral titers are typically highest and viral load was determined in lung tissue. FIG. 2 illustrates the statistically significant reduction (p<0.01) in viral titer in lung tissue that was observed in the 5 mg/kg rhCC10 dose group, and the trend towards a lower viral titer in the 0.5 mg/kg dose group. Viral titer in lung is expressed as (x $10^7$) TCID$_{50}$/gram of tissue.

Based on the foregoing, rhCC10 has been found to reduce viral titer in a respiratory infection, indicating the use of rhCC10 to treat, cure and/or prevent influenza infection. Accordingly, embodiments of the present invention provide an intranasal, and intravenous, or a combination rhCC10 based therapy effective at treating, curing or preventing influenza infection.

EXAMPLE 4

CC10-Mediated Inhibition of Viral Replication at the Cellular Level

Figure 3:
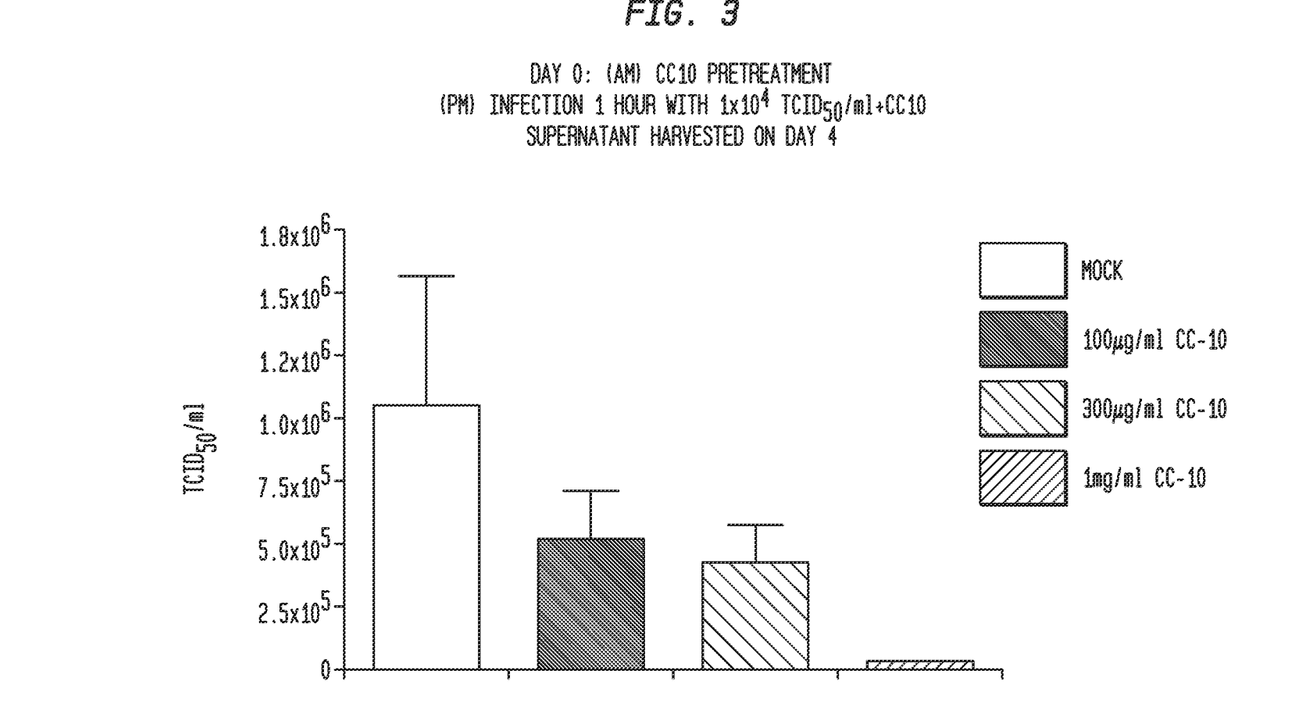
FIG. 3 is a bar graph depicting inhibition of viral replication in cultured cells by rhCC10. RhCC10 was added to the culture medium of HEp2 cells at 100 micrograms/ml, 300 micrograms/ml, and 1 milligram/ml and left for 4 hours. Then the medium was removed and replaced and cells were infected with RSV for 1 hour. The cells were then washed to remove excess virus and rhCC10 was added back and incubated for another hour. Then cells were washed to remove excess CC 10. Viral titers in culture medium were measured at 4 days post-infection. Each CC10 concentration was performed in triplicate.

HEp2 cells (ATCC, Manassas, Va.) were used to propagate RSV, strain A-2 (Advanced Biotechnologies, Inc., Columbia, Md.) and generate viral stocks. Cells were plated at 50,000 cells/well in 48 well plates and grown in MEM with 10% FBS to ~80% confluence. Cells were pre-treated with CC10 in 0.5 mL MEM for 4 hours. Medium was then changed and RSV infections were performed using 1×$10^6$ TCID$_{50}$ per 100 mm TC dish for 1 hour. Non-adsorbed virus was removed by washing and 0.5 ml of MEM with 2% FBS, 4 mM L-glutamine, and rhCC10 was added. Supernatants were collected on day 4 post infection and the virus titrated. FIG. 3 shows that a concentration of 1 mg/ml CC10 virtually eliminated RSV production, while 100 and 300 micrograms/ml showed a ~3-fold decrease.

Figure 4:
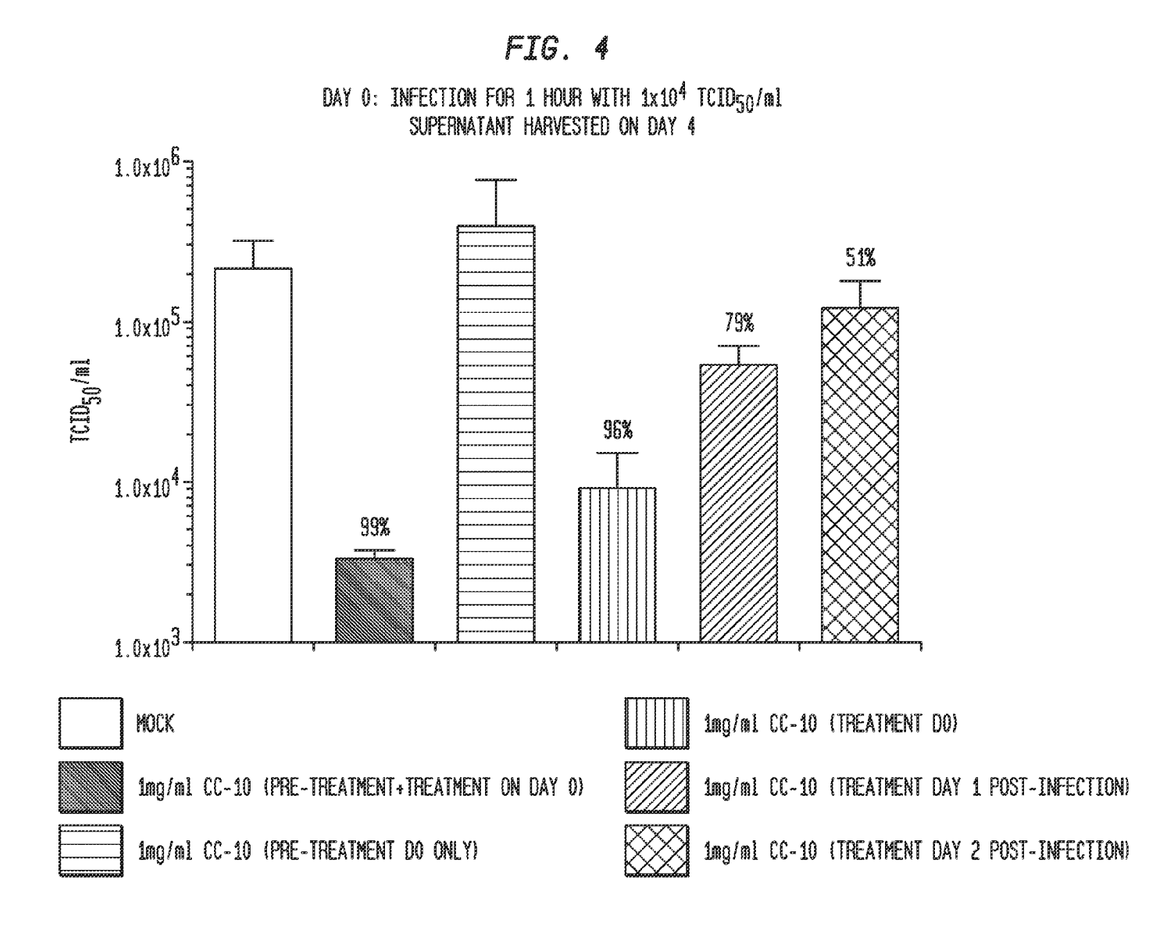
FIG. 4 is a bar graph comparison of rhCC10 antiviral effects when given pre-infection and post-infection. HEp2 cells were treated with 1 mg/ml rhCC10 and infected with RSV as in FIG. 3. In addition, 1 mg/ml of rhCC10 was given at one hour after infection (treatment D0), 24 hours after infection (treatment D1), and 48 hours after infection (treatment D2). Viral titers in culture media were measured on day 4 post-infection.

CC10 also inhibited viral replication in cells when given at 1, 24, and 48 hours after infection. FIG. 4 shows that rhCC10 is effective at reducing viral titer not only when added before infection, but also when added after infection. This is the first report of a direct anti-viral activity of CC10 at the cellular level and illustrates the potential utility of rhCC10 as an anti-viral therapy for post-exposure treatment.

EXAMPLE 5

CC10 Anti-Viral Mechanism of Action

The phenotype of airway epithelial cells in the CC10 knockout mouse illustrates that in the absence of CC10, the distribution of intracellular organelles is abnormal, that abnormal stacked membranous structures are present, and that secretion of other proteins made by the cell is disrupted. We surmise that this phenotype means that CC10 plays an active role in transport of secretory vesicles from the Golgi apparatus to the plasma membrane of the cell. CC10 also modulates the uptake and processing of antigens in antigen-presenting cells. We interpret these observations to mean that CC10 is an important factor in the transport of materials both out of and in to many types of cells. We therefore infer that CC10 inhibits viral replication by interfering with viral transport in the cell. Since all viruses rely upon cellular transport processes to invade the cell and replicate, CC10 can be expected to inhibit the replication of all viruses. Likewise, other secretoglobins, which share similar structure to CC10, can also be expected to inhibit viral replication at the cellular level. Similarly, peptides derived from CC10 and other secretoglobins that modulate cellular transport processes can also be expected to inhibit viral replication.

EXAMPLE 6

Bacterial Expression and Recovery of rhCC10

Figure 5:
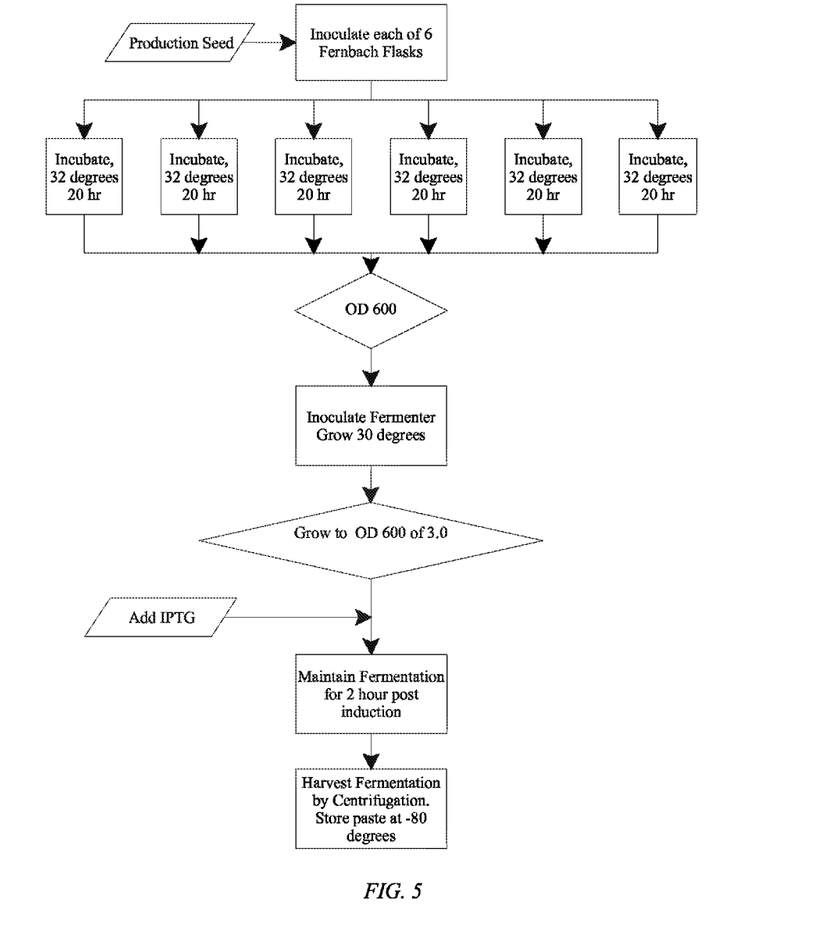
FIG. 5 is a summary schematic of rhCC10 expression in bacteria and recovery.

A summary schematic of the bacterial fermentation, expression of rhCC10, and harvest of cell paste containing rhCC10 is shown in FIG. 5. To begin the fermentation process, a vial of the Production seed cell bank was thawed at room temperature. One hundred microliters of the production seed was then used to inoculate each of the six, fernbach flasks containing one liter each of sterile Super Broth medium (Becton-Dickinson Select APS Super Broth, glycerol and WFI). The cultures in the six flasks were then incubated at 32° C. in a New Brunswick shaker-incubator with agitation (300 rpm) for approximately 20 hours. The cultures in the six flasks were then used to inoculate 300 liters of Superbroth in a 400 liter New Brunswick Scientific Fermenter System (Model IF-400). The culture was grown at 25° C. to 40° C. until a minimum optical density at 600 nm of 2.0 was reached. On reaching a minimum $OD_{600}$ of 2.0 the expression of rhUG is induced by the addition of isopropyl-β-Dthiogalactopyranoside (IPTG) to the fermentation culture to a final concentration of 0.1 mM to 10 mM. The fermentation was maintained for at least one hour, preferably two hours post induction. The bacterial culture is harvested by centrifugation with a Sharple's continuous feed centrifuge. The cell paste is partitioned and stored frozen at −80° C. for later purification.

EXAMPLE 7

Purification of rhCC10

Figure 6:
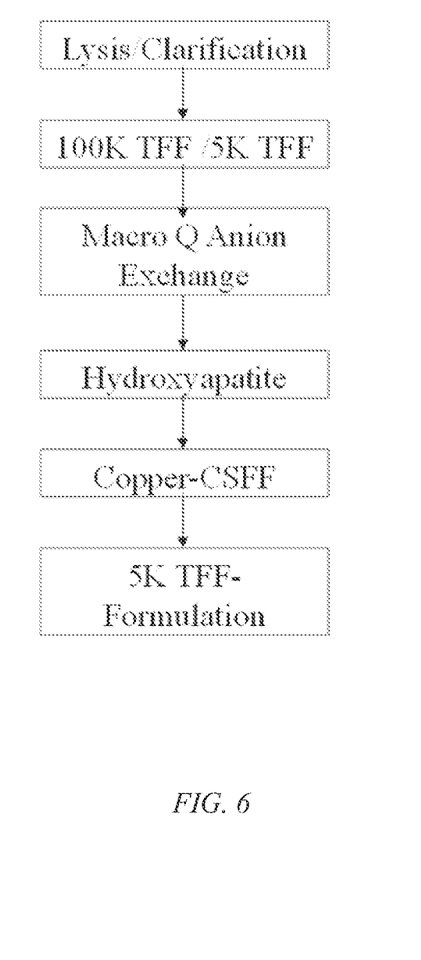
FIG. 6 is a schematic overview of an rhCC10 purification process.

An overview of the rhCC10 purification from bacterial cell paste is shown in FIG. 6. One kilogram of bacterial cell paste was lysed by shear and the cell debris removed by centrifugation. The lysate (supernatant) was then processed using a 100 K nominal molecular weight cut off (NMWCO) membrane in a tangential flow filtration (TFF) system. The permeate from the 100 K step was concentrated by TFF using a 5 K NMWCO membrane and loaded onto a Macro Q anion exchange column. The eluate from the anion exchange column was concentrated and diafiltered by TFF using a 5 K NMWCO membrane before being loaded onto a Type I Hydroxyapatite (HA) column. The eluate from the HA column was then loaded directly onto a column packed with Chelating Sepharose Fast Flow (CSFF) resin with copper as the chelate. The rhUG passed through the column while the host-derived proteins present in the HA eluate bound to the column. A positively charged Sartobind Q TFF membrane was also placed into the flowstream after the copper CSFF column to ensure that the maximum amount of endotoxin was removed from the final bulk material. The pass-through from the Sartobind Q was concentrated and then extensively diafiltered using a 5 K NMWCO membrane with saline for injection (SFI) as the replacement buffer, both to remove residual copper as well as to properly formulate the final bulk material.

EXAMPLE 8

Testing of rhCC10

The rhUG preparations made by this process, and minor variations thereof, are comparable in all respects: apparent size, molecular weight, charge, N-terminal amino acid sequence, amount of free thiol indicating correct formation of cystine-cystine bonds, immunological recognition techniques such as ELISA and Western blotting, and biological activity. Protein purified using the copper CSFF column was tested for the presence of copper by Inductively Coupled Plasma (by QTI Inc.). No copper was detected and the detection limit of the assay was 0.5 ppm.

The following assays were established as in process assays, characterization assays and release assays for the production process and for the drug substance and drug product. The rhUG drug substances and drug products were compared to standard research lot rhUG/7 where appropriate.

Bacterial Nucleic Acids. Bacterial DNA content per dose of the rhUG drug substance and drug product was determined by Southern blot using radiolabeled bacterial DNA followed by hybridization to blotted concentrated rhUG sample (Charles River Laboratories-Malvern).

Mass Spectroscopy. The molecular weight was determined by Electrospray Ionization spectrometry by M-Scan Inc. Theoretical molecular weight was determined by PAWS (a shareware program for the determination of average molecular mass, obtained through Swiss Pro). A value of 16110.6 Da was determined by the PAWS program. The same value was found for cGMP batches of rhUG and was confirmed by MS analysis of standard research lot rhUG/7 as a control (determined molecular weight 16110.6 Da).

N-terminal Sequence analysis. The sequence of the N-terminus was carried out using pulsed phase N-terminal sequencing on an Applied Biosystems (ABI) 477A automatic protein sequencer. The analysis was performed by M-Scan Inc. A sequence of Ala-Ala-Glu-Ile was confirmed for cGMP batches of rhUG with standard research lot rhUG/7 as a control. pH. A three-point calibration (4.0, 7.0, 10.0) is performed according to the manufacturers' instructions. After calibration of the electrode the pH of the sample is determined.

Isoelectric Focusing. The pI was determined by isoelectric focusing using gels with a pH range of 3 to 7. The gels were obtained from Novex and were run under conditions as described by the manufacturer. Samples were run versus a standard from Sigma and a rhUG control (research lot rhUG/7). Gels were fixed by heating in a microwave for 1 minute in the presence of 10% acetic acid/30% methanol followed by staining with Gel Code Blue stain from Pierce. Destaining was performed in purified water as described by Pierce. Free Thiol. The presence of free thiol was determined by reaction with Ellman's reagent from Pierce using a modified proticol to increase sensitivity. After incubation in the presence of Ellman's reagent the absorbance of samples was determined in the spectrophotometer at 412 nm. An extinction coefficient of 14150 M-1 cm-1 was used to determine the molar amount of free thiol. A standard curve of free thiol (cysteine) was used to monitor the linearity of the reaction.

LAL. The presence of bacterial endotoxin in rhUG process intermediates, drug substance and drug product was tested by the Limulus ameobocyte lysate assay as described in United States Pharmacopeia (USP) Assay No. 85. Kits were obtained from Associates of Cape Cod.

Color, Appearance, Homogeneity. The bulk drug product was visually inspected for clarity, color and visible particulate matter.

Purity and Identity: Reducing SDS PAGE. The rhUG drug substance and drug product was run on a Novex 10-20% Tricine SDS-PAGE gel under both reducing and non-reducing conditions as described by the manufacturer. Low molecular weight size standards were obtained from Amersham. Gels were fixed by heating in a microwave for 1 minute in a mixture of 10% acetic acid/30% methanol and stained with brilliant blue R250 (0.5%, w/v). Gels were destained with Novex Gel-Clear destaining solution as described by the manufacturer. Gels were then dried using the Novex Gel-Dry system and the percent purity was determined by scanning the gel (Hewlett-Packard scanner Model 5100C) and densitometry was performed using Scion Image shareware from the NIH.

Aggregation Assay. The drug product was analyzed for the presence of aggregates by chromatography on either a Superose 12 or a Sephadex 75 size exclusion chromatography (SEC) column (Amersham/Pharmacia). The column was run according to the manufacturer's instructions using the BioRad Biologic system and peak area was determined using EZLogic Chromatography Analysis software, also from BioRad. The percent aggregation was determined by comparing the total area of all peaks vs. the area of peaks eluting prior to the main UG peak.

Endotoxin. Endotoxin levels were tested by the rabbit pyrogenicity assay as described in the USP No. 151. An amount of rhUG equivalent to a single human dose was administered intravenously over a 10 minute period. Body temperature increase relative to the baseline predose temperature was monitored over the course of three hours. Acceptable results consist of no temperature rise equal to or greater than 0.5° C. over the baseline results.

Protein Content. The protein contents of the process intermediates, drug substance and product were determined by the absorbance at 280 nm using a Shimadzu 120 and an extinction coefficient of 2070 M-1 cm-1 as determined by Mantile et al. (Mantile, 1993).

Sterility. The sterility assay was performed as described in the USP No. 71. Samples were incubated into Fluid Thioglycolate Media (FTM) and Tripticase Soy Broth (TSB). Positive controls for TSB media were *C. albicans, A. niger,* and *B. subtilis.* Positive controls for FTM were *S. aureus, P. aeruginusa, C. sporogenes.*

Testing results for rhCC10 are summarized in Table 2 and wherein positive biological activity test referred to inhibition of $PLA_2$ activity in U.S. Patent App. Publication No.: 20030207795, and refers to suppression of viral replication in the present invention.

TABLE 2

Test results for Lot 0728

| Test | Result |
| --- | --- |
| Color | Clear, colorless |
| Appearance | No turbidity |
| Homogeneity | Homogeneous |
| Purity | 97.4% |
| Aggregation | 2.25% |
| Sterility | Sterile |
| Biological activity | Positive |
| Bacterial nucleic acid | <1.6 pg/mg |
| Mass spectroscopy | 16112.6 |
| pH | 6.82 |
| Isoelectric focusing | 4.7 |
| Free Thiol | <0.5% (w/w) |
| LAL | <.01 EU/mg |
| Copper | <16 μM |

EXAMPLE 9

Safety and Tolerability of Intranasal Adminstration of rhCC10

As part of the safety assessment for this proof of concept intranasal administration of rhCC10 in humans adverse events (AEs) and serious adverse events (SAEs) were monitored, recorded and reported. The clinical investigator was responsible for the detection and documentation of events meeting the criteria and definition of an AE or SAE. An AE is any untoward medical occurrence in a subject or a clinical investigation temporally associated with the use of the investigational drug whether or not the event is considered to have a causal relationship with the drug. In this trial, a pre-existing condition (i.e., a disorder present before the AE reporting period started and noted on the pre-treatment medical history/physical examination form) was not reported as an AE unless the condition worsened or episodes increased in frequency during the AE reporting period. Serious adverse events were defined as any untoward medical occurrence that, at any dose; 1) results in death, 2) is life-threatening, 3) requires hospitalization or prolongation of an existing hospitalization, 4) results in disability/incapacity, 5) is a congenital anomaly/birth defect, 6) is an important Other Medical Event (OME), and 7) all grade 4 laboratory abnormalities. The AE reporting period for began upon receiving the first dose of investigational medication and ended at the 2-week post discontinuation of investigational medication visit (follow-up visit).

No SAE's occurred during the study. Overall, a total of 15 adverse events were reported in subjects in both the placebo and rhCC10 treatment groups. All AEs were rated as mild in severity. In each group, 11 of 15 AEs were rated as non-assessable with respect to relatedness to study drug while four of 15 AEs in each group were rates as unlikely to be related to study drug. A summary of AEs for each patient receiving placebo is given in Table 6 and for those receiving rhCC10 at the time of the AE are given in Table 7.

TABLE 6

List of adverse events for patient receiving placebo

| Patient number | Description | Maximum intensity | Reported as serious? | Relationship to trial drug |
| --- | --- | --- | --- | --- |
| 6 | Headache | 1 = mild | 0 = No | 1 = unlikely |
| 12 | Gastric influenza | 1 = mild | 0 = No | 4 = not assessable |
| 12 | Gastric influenza | 1 = mild | 0 = No | 4 = not assessable |
| 15 | Ear pain | 1 = mild | 0 = No | 1 = unlikely |
| 15 | headache | 1 = mild | 0 = No | 4 = not assessable |
| 15 | fatigue | 1 = mild | 0 = No | 4 = not assessable |
| 15 | ear pain | 1 = mild | 0 = No | 4 = not assessable |
| 20 | Sore throath | 1 = mild | 0 = No | 4 = not assessable |
| 20 | Common cold | 1 = mild | 0 = No | 4 = not assessable |
| 25 | Headache | 1 = mild | 0 = No | 1 = unlikely |
| 26 | Sore throat | 1 = mild | 0 = No | 4 = not assessable |
| 27 | stomach ache | 1 = mild | 0 = No | 1 = unlikely |
| 29 | common cold | 1 = mild | 0 = No | 4 = not assessable |
| 31 | Fever | 1 = mild | 0 = No | 4 = not assessable |
| 38 | urticaria | 1 = mild | 0 = No | 4 = not assessable |

TABLE 7

List of adverse events for patient receiving rhCC10

| Patient number | Description | Maximum intensity | Reported as serious? | Relationship to trial drug |
| --- | --- | --- | --- | --- |
| 1 | Common cold | 1 = mild | 0 = No | 4 = not assessable |
| 2 | Common cold | 1 = mild | 0 = No | 1 = unlikely |
| 2 | Common cold | 1 = mild | 0 = No | 1 = unlikely |
| 7 | Sore throat | 1 = mild | 0 = No | 1 = unlikely |
| 16 | fatigue | 1 = mild | 0 = No | 4 = not assessable |
| 16 | fatigue | 1 = mild | 0 = No | 4 = not assessable |
| 23 | Headache | 1 = mild | 0 = No | 4 = not assessable |
| 23 | Common cold | 1 = mild | 0 = No | 4 = not assessable |
| 26 | Common cold | 1 = mild | 0 = No | 4 = not assessable |
| 28 | tired | 1 = mild | 0 = No | 4 = not assessable |
| 28 | tired | 1 = mild | 0 = No | 4 = not assessable |
| 28 | headache | 1 = mild | 0 = No | 4 = not assessable |
| 32 | Headache | 1 = mild | 0 = No | 4 = not assessable |

TABLE 7-continued

List of adverse events for patient receiving rhCC10

| Patient number | Description | Maximum intensity | Reported as serious? | Relationship to trial drug |
|---|---|---|---|---|
| 38 | ague | 1 = mild | 0 = No | 4 = not assessable |
| 39 | Mild cold | 1 = mild | 0 = No | 1 = unlikely |

Therefore, intranasal rhCC10 administration was found to be safe and well-tolerated in humans when given once daily as an aerosol in a divided dose of 1.1 milligrams, 0.56 milligrams per nostril, for seven consecutive days.

We claim:

1. A method of reducing the titer of influenza in lung tissue of a patient comprising; administering human CC10 or rhCC10 to the patient wherein the titer of influenza in the lung tissue of the patient is reduced.

2. The method of claim 1 wherein the rhCC10 treats an influenza infection in the patient.

3. The method of claim 1 wherein the influenza is Type A influenza.

4. The method of claim 1 wherein the influenza is the H1N1 strain of influenza.

5. The method of claim 1 wherein the human CC10 or rhCC10 is administered by the intranasal route.

6. The method of claim 1 wherein the human CC10 or rhCC10 is administered by the intravenous route.

7. The method of claim 1 wherein the human CC10 or rhCC10 is administered by a combination of intranasal and intravenous routes.

* * * * *